United States Patent [19]

Miller

[11] Patent Number: 4,658,083
[45] Date of Patent: Apr. 14, 1987

[54] STRAINS OF PLEUROTUS
[75] Inventor: Liliane Miller, Tours, France
[73] Assignee: Somycel, France
[21] Appl. No.: 715,128
[22] Filed: Mar. 22, 1985
[30] Foreign Application Priority Data
Mar. 23, 1984 [FR] France .................. 84 04549
[51] Int. Cl.⁴ .............................. A01G 1/04
[52] U.S. Cl. .......................... 800/1; 47/1.1
[58] Field of Search ................. 47/1.1; 800/1

[56] References Cited
U.S. PATENT DOCUMENTS
4,242,832 1/1981 Eger et al. .................. 47/1.1

Primary Examiner—Robert E. Bagwill
Attorney, Agent, or Firm—Darby & Darby

[57] ABSTRACT

Sporeless pleurotus strains having lamellae decurrent over the major part of the foot and lamellae more developed than those of the other known Pleurotus strains.

7 Claims, 2 Drawing Figures

STRAINS OF PLEUROTUS

The invention relates to new strains of sporeless mushrooms of the genus pleurotus. Cultivation of these mushrooms is entirely free of the nuisances to growers provoked by the presence of spores.

The pleurotus is a well-known edible mushroom, remarkable in particular for the very large quantity of spores that it releases. These spores are allergenic to man. Furthermore, the spores are vectors that can transmit viruses from one culture to another and interfere with the growth of pleurotus.

The essential object of the present invention is to propose new stocks of pleurotus lacking the drawbacks connected with the presence of very numerous spores.

Another object of the invention is to provide strains of pleurotus which are of particular economic interest by reason of their increased yield.

The invention is directed to new strains of pleurotus characterized in that they have:

a sporeless character, decurrent lamellae over the major part of the height of the foot, lamellae more developed than those of other strains of pleurotus.

The present pleuroteus mushrooms generally have less than about ten spored basidia per lamella.

Their spores can germinate and the homokaryotic mycelium issuing from the spores carries the "sporeless" gene.

Other aspects of the invention are:

A strain of sporeless pleurotus identified as the strain SOMYCEL 3.200, characterized in that it results from the crossing of the homokaryons PZ 21.3 and PZ 15 al;

A pleurotus of the strain SOMYCEL 3.200 characterized in that its carpophore has a massive, erect foot and a well developed, fleshy and heavy cap;

A strain of sporeless pleurotus, identified as the strain SOMYCEL 3.210, characterized in that it results from the crossing of the homokaryons PZ 25 a6 and PZ 15 al; and A pleurotus of the strain SOMYCEL 3.210 characterized in that its carpophore has a fine, very long foot; a small, light, not very fleshy cap with axial symmetry and shaped like a cornet (horn); and a flaw of geotropism.

The new sporeless pleurotus strains according to the invention, whether of the SOMYCEL 3.200 strain or the SOMYCEL 3.210 strain, have a number of characteristics in common and a few characteristics of their own.

PHYSIOLOGICAL CHARACTERISTICS

Common Characteristics

In contrast to the other, known, pleurotus strains, the pleurotus stocks according to the invention are sporeless in character, that is to say that they have few spores: generally less than about ten spored basidia per lamella. These spores can germinate and the homokaryotic mycelium issuing from the spores bears the "sporeless" gene. Their need for light is greater than that of the known strains, but in intensity rather than in time of exposure. They fructify within a temperature range betweeen 5° and 20° C.

Special Characteristics

For the strain SOMYCEL 3.200, the optimal fructification lies between 12° and 18° C. At 12° the yield in a normal production cycle is greater by about 40% than that of the known strain SOMYCEL 3.004 (*Pleurotus ostreatus*).

For the strain SOMYCEL 3.210, the optimum fructification lies between 10° and 15° C. At 12° C. the yield in a normal production cycle is about 50% higher than that of the strain SOMYCEL 3.004.

Thus, a yield considerably higher than the average, based on the SOMYCEL 3.004 strain is manifest.

MORPHOLOGICAL CHARACTERISTICS

Common Characteristics

The pleurotus strains according to the invention are particularly remarkable for their lamellae which are very wide.

The lamellae are decurrent over the major part of the height of the foot. The foot exhibits a loose and lacunar tissue.

Special Characteristics

Figure 1:
FIGS. 1 and 2 depict the morphological characteristics of two new pleurotus mushrooms according to the invention.

For the strain SOMYCEL 3.200, the cap is generally eccentric relative to the foot, but it can assume a cornet shape with axial symmetry, or a curled shape. It is well developed, flashy and heavy. The foot is erect and massive, the lamellae are decurrent to practically the base of the foot, and the general color varies from light grey to chestnut, as shown in FIG. 1.

Figure 2:
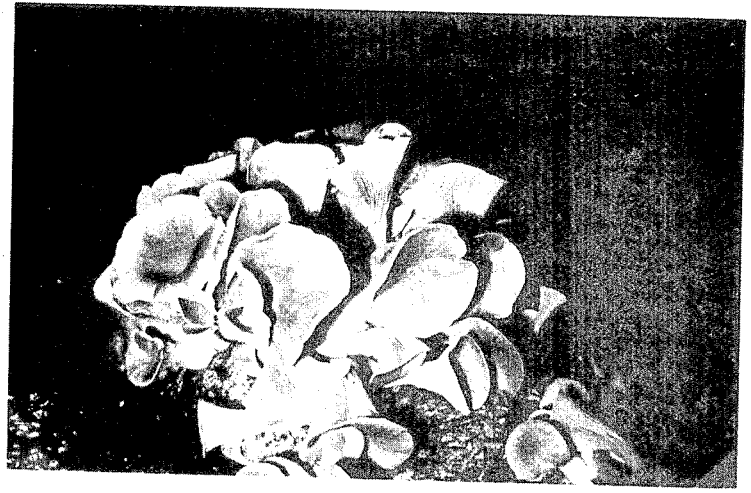

For the strain SOMYCEL 3.210 the cap has a cornet or trumpet shape, with axial symmetry. It is small, not very fleshy, and light. The foot is fine and very long. The lamellae are decurrent over about two thirds of the height of the foot. The general color is grey. This pleurotus is also characterized by a flaw of geotropism and by the fact that it falls back to the ground, as shown in FIG. 2.

GENETIC CHARACTERISTICS

The genetic origin of the two strains is common: it arises from the neohaplont 42 which is "sporeless" in character, obtained by dedikaryotization according to the U.S. Pat. No. 4,242,832 of Eger and the French Pat. No. FR-A-2,420,914, both incorporated by reference. The procedure consists of a crossing of the neohaplont 42 with the strain SOMYCEL 3.004 and from this crossing the homokaryons bearing the "sporeless" character, identified as homokaryons Z EGER are selected. Then these "sporeless" Z EGER homokaryons are crossed with the stock SOMYCEL 3.030 (also *Pleurotus ostreatus*). From this cross, the homokaryons bearing the "sporeless" character, identified as homokaryons PZ are selected. The homokaryons PZ 21.3 and PZ 15 al are crossed with one another to obtain the strain SOMYCEL 3.200, and the homokaryons PZ 25 a6 and PZ 15 al are crossed to obtain the strain SOMYCEL 3.210.

It is to be noted that the homokaryhons do not constitute a complement with the "sporeless" testers 42 and 11 mentioned in French Pat. No. FR-A-2.420.914 and U.S. Pat. No. 4,242,832.

The incompatibility factors are: a3 b3 originating in strain 42 and al b7 originating, respectively, in the strain SOMYCEL 3.004 for al and the strain SOMYCEL 3.030 for b7.

Finally, by back-crossing with the strain SOMYCEL 3.030, the homokaryons go back to the wild type 3.030 for the color and the shape of the mushroom Dedikaryotization of the strains SOMYCEL 3.200 and SOMYCEL 3.210, produces the neohaplonts having the preceding characteristics.

It will be noted that the new pleurotus strains according to the invention have a certain number of new characteristics, for example: sporelessness lamellae decurrent over the major part of the height of the foot, and lamellae more developed than those of the other strains of pleurotus.

The pleurotus of the strain SOMYCEL 3.210 also has a trumpet shape and a flaw of geotropism.

What is claimed is:

1. Sporeless pleurotus strains comprising:
lamellae decurrent over a major portion of the height of the pleurotus foot,
lamellae more developed than those of the other pleurotus strains.

2. Pleurotus strains according to claim 1, comprising less than about ten spored basidia per lamella.

3. Pleurotus strains according to claim 2, said strains having spores capable of germinating with the homokaryotic mycelium issuing from the spores bearing the sporeless gene.

4. Pleurotus strain according to claim 1 said strain resulting from the crossing of homokaryons PZ 21.3 and PZ 15 a1.

5. Pleurotus of the strain according to claim 4, having a carpophore comprising a massive, erect foot, and a well-developed fleshy and heavy cap.

6. A strain of pleurotus according to claim 1, said strain resulting from the crossing of homokaryons PZ 25 a6 and PZ 15 a1.

7. Pleurotus strain according to claim 6, having a carpophore comprising a fine, very long foot; a small, light and not very fleshy cap, with axial symmetry and shaped like a cornet; and a flaw of geotropism.

* * * * *